United States Patent [19]
Lin

[11] Patent Number: 5,376,126
[45] Date of Patent: Dec. 27, 1994

[54] ARTIFICIAL ACETABULAR JOINT REPLACING DEVICE

[76] Inventor: Chih-I Lin, 513 S. Golden Pardos Dr., Diamond Bar, Calif. 10765

[21] Appl. No.: 151,015

[22] Filed: Nov. 12, 1993

[51] Int. Cl.⁵ .................. A61F 2/32; A61F 2/36; A61F 5/04
[52] U.S. Cl. ........................ 623/23; 623/22; 623/18; 606/60
[58] Field of Search .............. 623/16, 18, 19, 22, 623/23; 606/60, 61, 63, 65, 67, 70, 72, 74

[56] References Cited

U.S. PATENT DOCUMENTS 5,007,935  4/1991  Vingent et al. ............ 623/22

FOREIGN PATENT DOCUMENTS 0245846  11/1987  European Pat. Off. ....... 623/23
2674122   9/1992  France ................... 623/23
2724234  12/1977  Germany .................. 623/23
3607824   9/1987  Germany .................. 623/23
1572603   6/1990  U.S.S.R. ................. 623/22

Primary Examiner—David Isabella
Attorney, Agent, or Firm—Bacon & Thomas

[57] ABSTRACT

An artificial acetabular joint replacing device includes an acetabular joint replacing body, an acetabular cap, a fastening piece, one or more fastening screws, and one or more fastening cords. The acetabular joint replacing body is dimensioned to fit over a premended portion of a femur and provided in the bottom portion thereof with at least one cord hole and one or more fastening holes. The fastening piece is provided with one or more fastening holes and cord holes. The fastening screws are used to fasten together the acetabular joint replacing body, the femur and the fastening piece by engaging the fastening holes of the acetabular joint replacing body and the fastening piece, and predrilled fastening holes of the femur. The fastening cords are used to reinforce the fastening of the acetabular joint replacing body, the femur and the fastening piece by passing through the cord holes of the acetabular joint replacing body and the fastening piece.

5 Claims, 3 Drawing Sheets

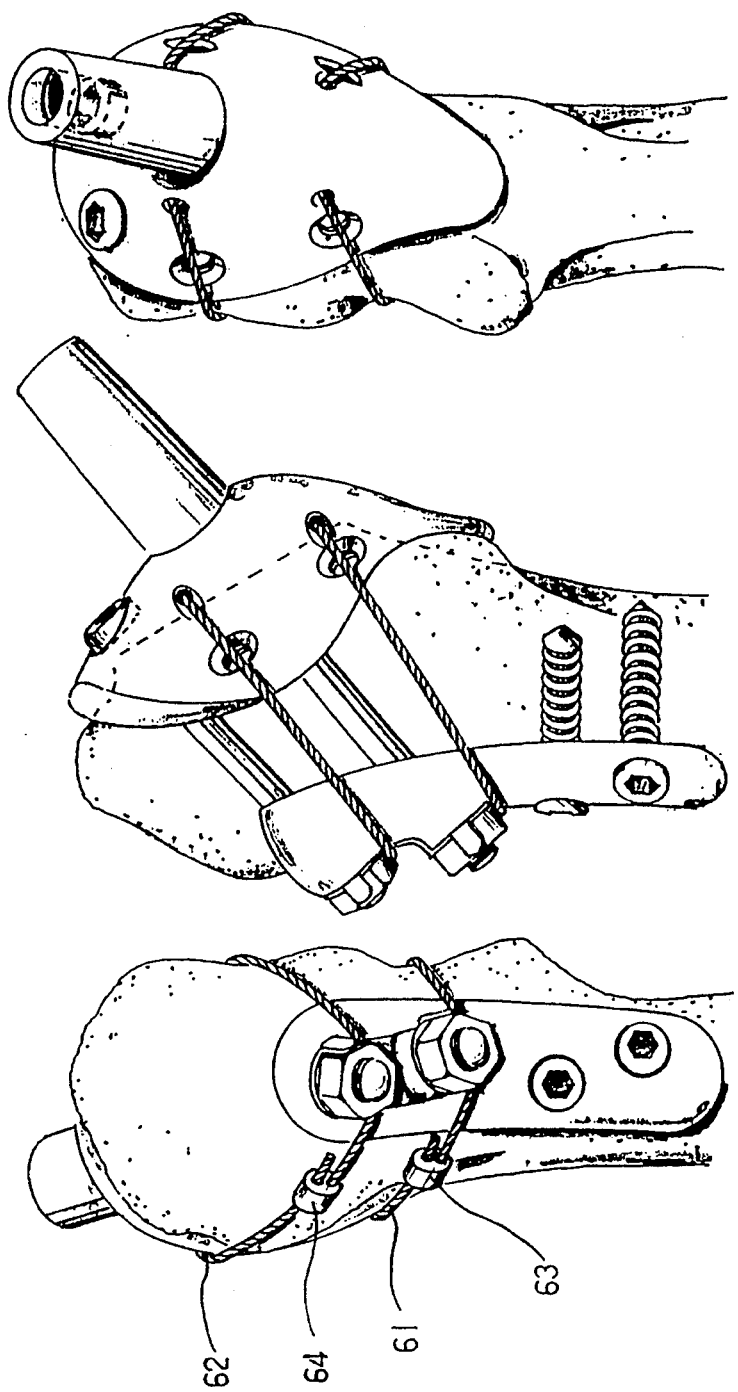

ARTIFICIAL ACETABULAR JOINT REPLACING DEVICE

FIELD OF THE INVENTION

The present invention relates to an artificial acetabular joint replacing device.

BACKGROUND OF THE INVENTION

The artificial acetabular joint replacing device of the prior art is generally composed of a femoral stem and an acetabular cup, as exemplified by the acetabular joint combination system of the Zimmer Corporation of the United States. Such a conventional device as described above is defective in design in that the femoral stem often fails to join intimately with the femur to which the femoral stem is fastened, thereby resulting in a gradual descent of the femoral stem. Such a surgical mishap often calls for another aggravating surgical operation in which a new acetabular joint combination system is set in place.

SUMMARY OF THE INVENTION

It is therefore the primary objective of the present invention to provide an artificial acetabular joint replacing device, which overcomes the shortcoming of the artificial acetabular joint replacing device of the prior art described above.

A further objective of the present invention is to provide an artificial acetabular joint replacing device consisting of an acetabular joint replacing body serving as a main body of the device, an acetabular cap, a fastening piece, one or more fastening screws, and one or more fastening cords.

In keeping with the principle of the present invention, the foregoing objectives of the present invention are attained by the artificial, acetabular joint replacing device which comprises: an acetabular joint replacing body having a top portion provided with a receiving neck and further having a bottom portion adapted to fit over a premended femur, the bottom portion being provided with at least one cord hole and one or more fastening holes; an acetabular cap having a bottom adapted to be mounted on the receiving neck of the acetabular joint replacing body and having a top adapted to be fastened to the acetabular joint; a fastening piece provided with one or more fastening holes and located on another side of the femur opposite to the side to which the acetabular joint replacing body is attached; one or more fastening screws engaging the one or more fastening holes of the fastening piece, the predrilled fastening holes of the femur, and one or more fastening holes of the bottom portion of the acetabular joint replacing body such that the fastening piece, the femur and the acetabular joint replacing body are united; and one or more fastening cords adapted to pass through the at least one cord hole of the fastening piece and at least one cord hole of the bottom portion of the acetabular joint replacing body for tightening up the connection of the fastening piece, the femur and the acetabular joint replacing body.

In one of the preferred embodiments of the present invention, the acetabular joint replacing body has a cup-shaped bottom portion provided with a fastening lug at its rim. The fastening lug is in turn furnished with at least one cord hole and one or more fastening holes.

In another one of the preferred embodiments of the present invention, the receiving neck of the acetabular joint replacing body is provided a sinking fastening hole at the center of the receiving neck.

The foregoing objectives, features and functions of the present invention can be more readily understood by studying the following detailed description of the preferred embodiments of the present invention in conjunction with the drawings provided herewith.

BRIEF DESCRIPTION OF THE DRAWINGS

FIGS. 2d–2f show schematic views taken from different directions of the second preferred embodiment of the present invention, as shown in FIGS. 2a–2c, with the fastening cords fastened thereto.

DETAILED DESCRIPTION OF THE INVENTION

Figure 1:
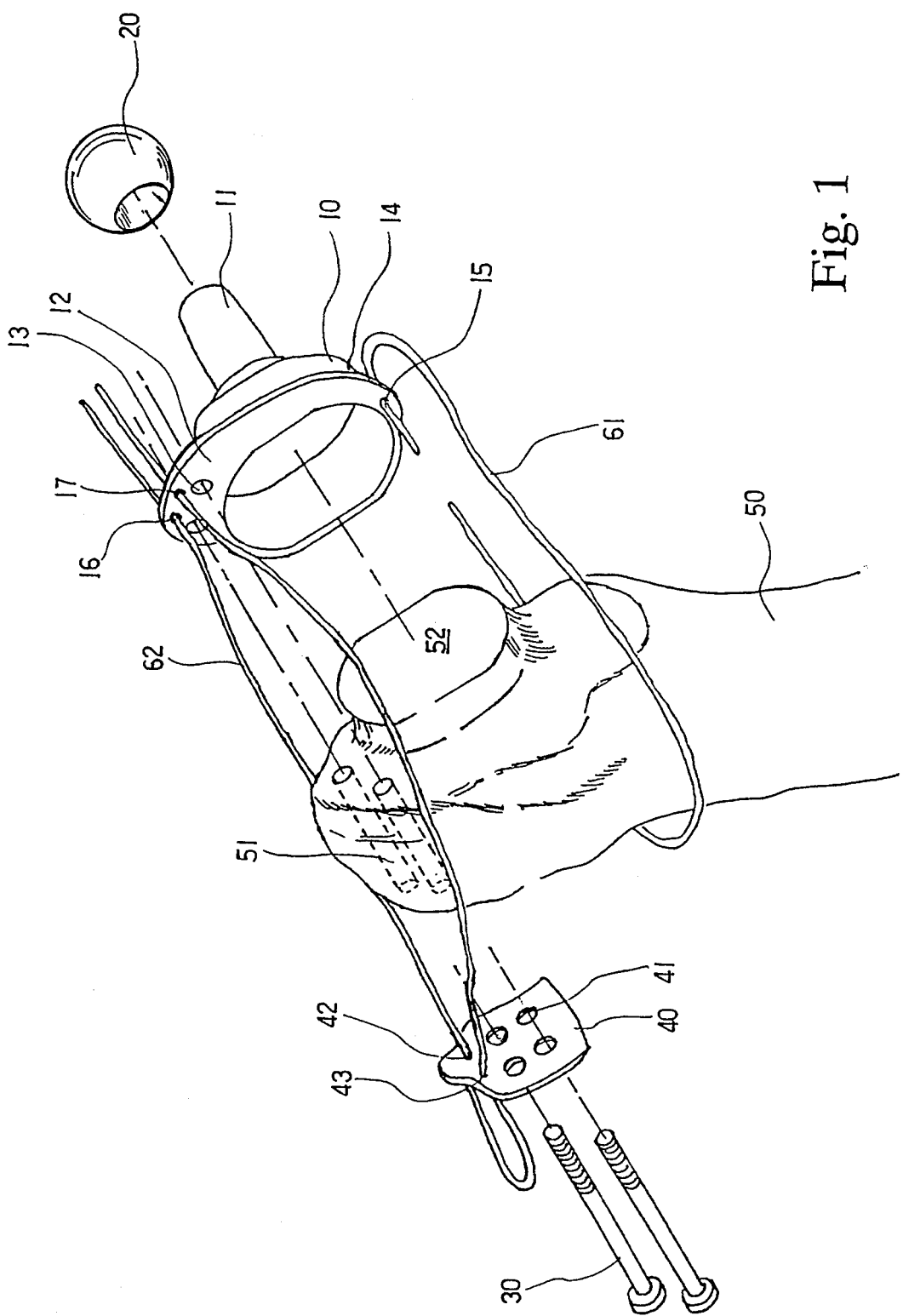
FIG. 1 shows an exploded view of a first preferred embodiment of the present invention.

As shown in FIG. 1, the first preferred embodiment of the present invention comprises an acetabular joint replacing body 10, an acetabular cap 20, two fastening screws 30, a fastening piece 40, and two fastening cords 61 and 62.

The acetabular joint replacing body 10 is provided on the top thereof with a receiving neck 11 having a top that receives the acetabular cap 20. The acetabular joint replacing body 10 has a cup-shaped bottom portion which is provided a fastening lug 12 at its rim 14 thereof. The fastening lug 12 has a plurality of cord holes 15, 16 and 17, and two fastening holes 13. The fastening piece 40 is provided with four fastening holes 41 engageable with the fastening screws 30. In addition, the fastening piece 40 is provided with two cord holes 42 and 43. A femur 50 is shown to comprise one or more predrilled fastening holes 51 and a premended portion 52. Each fastening screw 30 includes a bolt having a threaded portion at one end and an enlarged head at another end thereof, and a nut (not shown in FIG. 1). The threaded end of the bolt is inserted into the fastening hole 41 of the fastening piece 40, the predrilled fastening hole 51 of the femur 50 and passed through the fastening hole 13 of the fastening lug 12. The nut is then threadedly engaged with the threaded portion of the bolt of the fastening screw 30 such that the fastening piece 40, the femur and the acetabular joint replacing body 10 are united. The fastening cord 61 is put through the cord hole 15 of the fastening lug 12 such that the fastening cord 61 circumvents the femur 50. The fastening cord 62 is further put through the cord holes 16 and 17 of the fastening lug 12 and the cord holes 42 and 43 of the fastening piece 40 such that the fastening cord 62 circumvents the femur. The cup-shaped bottom portion of the acetabular joint replacing body 10 is dimensioned to fit over the premended portion 52 of the femur.

The fastening lug 12 may be of any shape and may constitute a fastening flange which is dimensioned to circumvent the entire acetabular joint replacing body 10 and provided in the appropriate positions thereof with a plurality of fastening holes, preferably two to four depending on the surgical requirements. The fastening holes 13 of the fastening lug 12 or the fastening flange may be threaded or nonthreaded.

The number of fastening screws 30 is not fixed, preferably two to four.

The fastening piece 40 may be of any shape, preferably a long bar shape. In addition, the fastening piece 40 may be replaced by a larger fastening piece or a plurality of fastening pieces which are fastened at relative positions.

The method of tightening up the acetabular joint replacing body 10, the femur 50 and the fastening piece 40 by means of the fastening cords 61 or 62 is similar to any conventional binding method. For example, a retaining member 63 or 64 shown in FIG. 2d can be used to fasten the fastening cords 61 or 62. For example, each end of the fastening cord 62 is put through each hole of the retaining member 63, each of which is then so moved as to cause the fastening cord 62 to hold securely the acetabular joint replacing body 10, the femur 50 and the fastening piece 40. With a hand tool, the retaining member 63 is subsequently caused to deform so as to hold securely the fastening cord 62.

Figures 2A, 2B, 2C:
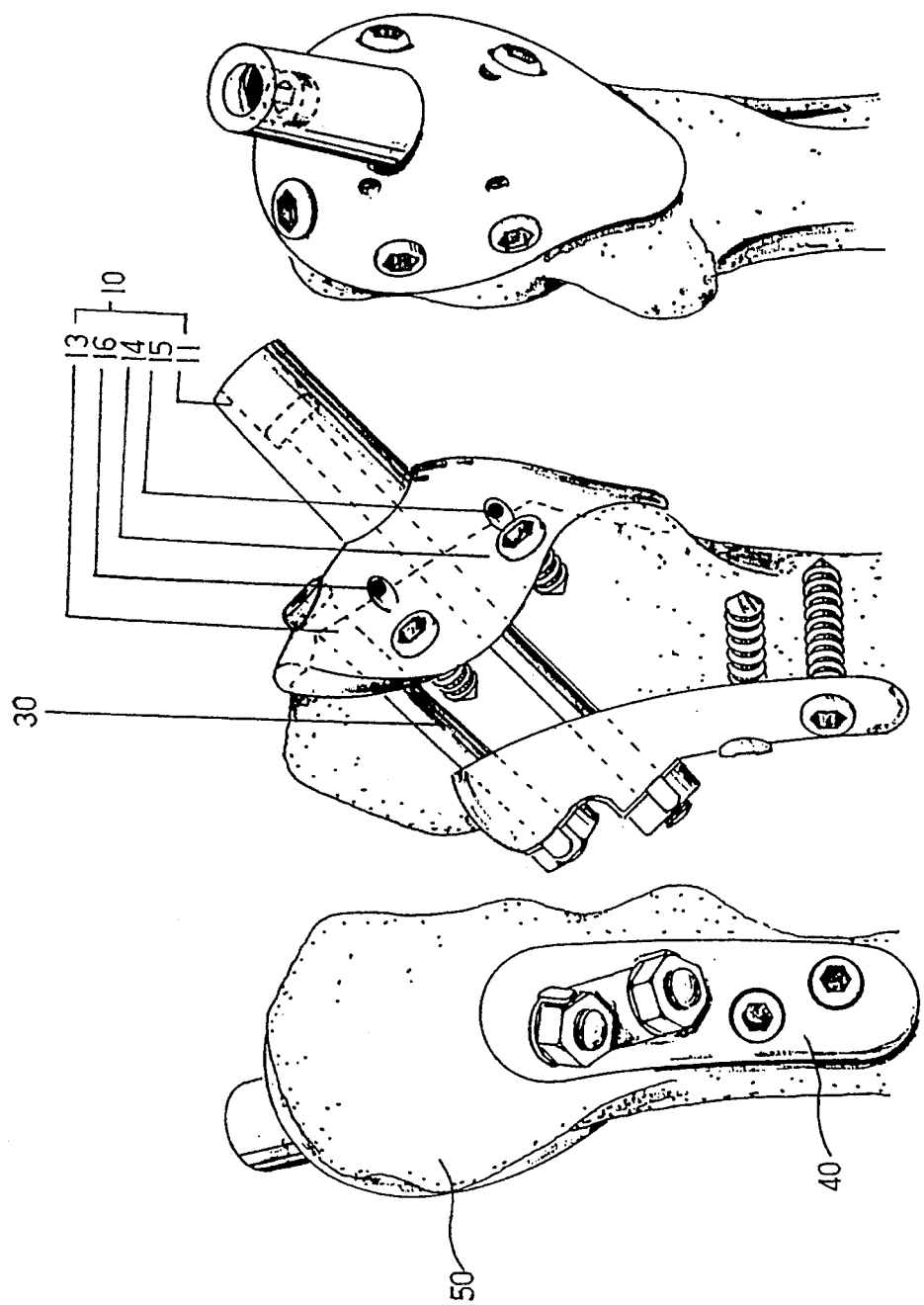
FIG. 2a–2c show schematic views taken from different directions of a second preferred embodiment of the present invention without the fastening cords fastened thereto.

The second preferred embodiment of the present invention is schematically illustrated in FIGS. 2a-2f, in which the reference numerals are similar in definition to those of FIG. 1. The fastening piece 40 used in the second preferred embodiment of the present invention as shown in FIG. 2a is devoid of the cord holes. As a result, the nuts of the fastening screws 30 are used to hold the fastening cords 61 and 62 firmly in place so as to prevent the fastening cords 61 and 62 from sliding (FIGS. 2d-2e). Moreover, the receiving neck 11 of the acetabular joint replacing body 10 of the second preferred embodiment of the present invention is provided a sinking fastening hole engageable with the fastening screw means 30 (FIG. 2b).

The method of tightening up the acetabular joint replacing body 10, the femur 50 and the fastening piece 40 by means of the fastening cords 61 or 62 is similar to any conventional binding method. As discussed above, two regaining members 63 and 64 shown in FIG. 2d are used to fasten the fastening cords 61 and 62.

The acetabular joint replacing body 10 and the fastening piece 40 of the second preferred embodiment of the present invention are fastened further securely with the femur 50 by means a plurality of bone screw nails, which are received in a plurality of bone screw nail holes provided on the acetabular joint replacing body 10 and the fastening piece 40 and are then fastened onto the femur 50. The bone screw nail holes may be either threaded or nonthreaded.

The acetabular joint replacing system of the present invention is made of any material suitable for use in an orthopedic surgery, such as implantable iron-based stainless 316LVM, Ti-6-4, cobalt-molybdenum alloy, or ceramic material sold by TDI Medical Corporation of USA under the trademark BIOLOX ®.

The acetabular cap 20 of the present invention may be any suitable acetabular cap, such as the palcartype acetabular cap or the standard type acetabular cap, both of which are made by the Zimmer Corporation of the United States.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What is claimed is:

1. An artificial acetabular joint replacing device comprising:
   an acetabular joint replacing body having a top portion provided with a receiving neck and further having a bottom portion adapted to fit over a femur that has been pre-drilled with at least one fastening hole extending therethrough, said bottom portion being provided with at least one cord hole and at least one fastening hole;
   an acetabular cap having a bottom adapted to be mounted on the receiving neck of the acetabular joint replacing body and having a top adapted to be fastened to an acetabular joint;
   a fastening piece having at least one fastening hole formed therein, said fastening piece being shaped to be located on a side of the femur opposite to the side to which the acetabular joint replacing body is attached;
   fastening screw means extending through said at least one fastening hole of the fastening piece, the at least one predrilled fastening hole of the femur, and said at least one fastening hole of the bottom portion of the acetabular joint replacing body such that the fastening piece, the femur and the acetabular joint replacing body are united; and
   at least one fastening cord adapted to pass through said at least one cord hole of the bottom portion of the acetabular joint replacing body, extend about the femur and engage said fastening plate for tightening up the connection of the fastening piece, the femur and the acetabular joint replacing body.

2. The artificial acetabular joint replacing device of claim 1 wherein the bottom portion of the acetabular joint replacing body is cup-shaped and includes a fastening flange at a rim portion thereof, said at least one cord hole and said at least one fastening hole of said acetabular joint replacing body extending through the fastening flange.

3. The artificial acetabular joint replacing device of claim 1 wherein the receiving neck of the acetabular joint replacing body includes a sinking fastening hole at a center portion thereof.

4. The artificial acetabular joint replacing device of claim 1 wherein said fastening screw means comprises a bolt having a threaded portion at one end and an enlarged head at another end thereof, and a nut.

5. The artificial acetabular joint replacing device of claim 1 wherein said fastening plate further includes at least one cord hole through which said at least one fastening cord extends.

* * * * *